US005188840A

United States Patent [19]
Iida et al.

[11] Patent Number: 5,188,840
[45] Date of Patent: Feb. 23, 1993

[54] SLOW-RELEASE PHARMACEUTICAL AGENT

[75] Inventors: Yoshimitsu Iida, Saitama; Shuji Sumida, Tokyo, both of Japan

[73] Assignee: Chugai Seiyaku Kabushiki Kaisha, Tokyo, Japan

[21] Appl. No.: 906,959

[22] Filed: Sep. 15, 1986

[30] Foreign Application Priority Data

Sep. 26, 1985 [JP] Japan ................................ 60-213277

[51] Int. Cl.$^5$ ............................................. A61K 9/22
[52] U.S. Cl. .................... 424/468; 424/471; 424/472
[58] Field of Search ............. 424/458, 472, 468, 462

[56] References Cited

U.S. PATENT DOCUMENTS

| | | | |
|---|---|---|---|
| 3,577,491 | 5/1971 | Cox | 264/120 |
| 3,608,063 | 9/1971 | Banker | 424/485 |
| 3,882,228 | 5/1975 | Boncey et al. | 424/489 |
| 3,903,255 | 9/1975 | Gusman et al. | 424/44 |
| 3,943,238 | 3/1976 | Kobayashi et al. | 424/452 |
| 3,993,999 | 1/1976 | Craps | 424/482 X |
| 4,021,546 | 5/1977 | Bodor | 536/6.1 |
| 4,153,702 | 5/1979 | Hörlein et al. | 514/316 X |
| 4,180,559 | 12/1979 | Huber | 424/480 |
| 4,193,985 | 3/1980 | Bechgaard et al. | 424/462 X |
| 4,342,764 | 8/1982 | Ilvespaa et al. | 514/326 X |
| 4,389,403 | 6/1983 | May et al. | 514/314 |
| 4,406,896 | 9/1983 | Higuchi et al. | 514/200 X |
| 4,503,031 | 3/1985 | Glassman | 424/471 X |
| 4,530,920 | 7/1985 | Nestor et al. | 514/15 |
| 4,582,834 | 4/1986 | Stenzel | 514/274 |
| 4,894,424 | 1/1990 | Geoghegan et al. | 424/489 |

FOREIGN PATENT DOCUMENTS

| | | |
|---|---|---|
| 0123740 | 10/1984 | European Pat. Off. |
| 0185347 | 6/1986 | European Pat. Off. |
| 2027325 | 12/1970 | Fed. Rep. of Germany |
| 2841170 | 3/1980 | Fed. Rep. of Germany |
| 1037689 | 2/1964 | United Kingdom |
| 2123291 | 1/1984 | United Kingdom |

OTHER PUBLICATIONS

Remington's Pharmaceutical Sciences Treatise, 17th Edition (1985), pp. 1603-1604.

Primary Examiner—Thurman K. Page
Assistant Examiner—D. Colucci
Attorney, Agent, or Firm—Browdy and Neimark

[57] ABSTRACT

A slow-release pharmaceutical agent which comprises fumaric acid and/or DL-tryptophan in addition to one or more pharmaceutically active substances, and a process for preparation of the same are disclosed. Among many organic acids and amino acids, fumaric acid and DL-tryptophan are remarkably useful for extending the duration of release of a pharmacologically active substance when fumaric acid, DL-tryptophan or both is used for formulation of a pharmaceutical agent. The pharmaceutical agent may be in any solid form of formulations such as powder, granule, tablet, troche, capsule, suppository, etc., and may be used with practically all types of drugs.

38 Claims, 7 Drawing Sheets

THE RELATIONSHIP OF DISSOLUTION TIME AND
THE RATIO OF FUMARIC ACID TO DL-TRYPTOPHAN

SLOW-RELEASE PHARMACEUTICAL AGENT

BACKGROUND OF THE INVENTION

While many compounds are known to be useful as pharmacologically active substances, some of them have relatively short biological half lives and must be administered several times a day in order for their full action to be exhibited. However, a decrease in the number of administrations will not only reduce the burden on the patient but will also increase his compliance and thus provide greater therapeutic effects In order to meet this requirement, medicines must release their active ingredients slowly so that they maintain effective levels in the blood, for a prolonged period of time Therefore, the principal object of the present invention is to provide a pharmaceutical agent which is so designed that it will slowly release its active substance over a period of time.

Various techniques have been proposed for preparing slow-release pharmaceutical agents that are capable of retaining the concentrations of their active substances in the blood for a prolonged period of time. Most of the slow-release pharmaceuticals so far proposed employ a variety of high-molecular weight materials which include: hydroxypropyl cellulose, hydroxypropyl methyl cellulose, hydroxypropyl methyl cellulose phthalate, pullulan, gelatin, collagen, casein, agar, gum arabic, dextrin, ethyl cellulose, methyl cellulose, chitin, chitosan, mannan, carboxymethylethyl cellulose, sodium carboxymethyl cellulose, polyethylene glycol, sodium alginate, poly(vinyl alcohol), cellulose acetate, poly(vinylpyrrolidone) silicone, poly(vinyl acetal) diethylamino acetate and albumin [see Sustained and Controlled Release Drug Delivery Systems, Marcel Dekker, Inc., 1978; Yakkyoku (Pharmacy), vol. 35, No. 2, pp 575-583, 1984; and Japanese Patent Public Disclosure No. 62521/1984].

The use of the above-listed high-molecular weight materials in manufacturing slow-release pharmaceuticals have several problems: (1) many high-molecular weight materials, particularly those which are soluble in water, have such a high moisture content that the pharmacologically active substances incorporated therein are liable to suffer decomposition, such as by hydrolysis, and often fail to withstand prolonged storage; (2) high-molecular weight materials have distributions in molecular weight and their molecular weight distribution and average molecular weight generally differ from one to another notwithstanding the existence of certain limits to be complied with and, therefore, the slow-release pharmaceuticals employing such high-molecular weight materials will experience considerable variations in drug dissolution rate no matter how strict the quality control is during the manufacturing process; (3) some of the slow-release pharmaceuticals employing high-molecular weight materials are used while they are implanted in the human body, but many high-molecular weight materials are not decomposed in the human body at all or are decomposed only slightly, so they must be removed from the human body after they have liberated the pharmaceutically active substance; even the high-molecular weight materials that are decomposable in the human body are in most cases dependent upon the presence of decomposition enzymes if the rate of their decomposition is to be satisfactory, and this applies to the rate of release of the active substance too; furthermore, even the decomposable high-molecular weight materials are not completely decomposed to monomers and there is a high possibility that only a part of them are decomposed, most of them remaining as polymers and being absorbed by tissues to become a potential antigen capable of causing an anaphylactic shock [see Seiyaku Kojo (Pharmaceutical Factory), vol. 13, No. 10, pp. 552-557 (1983); and Kagaku no Ryoiki (Region of Chemistry), Special Issue, No. 134, pp. 151-157, Nankodo]; and (4) in slow-release pharmaceuticals of the matrix type and those wherein the active substances (i.e., drugs) are released through a semipermeable membrane, the drug release rate is so highly dependent on the solubility of the drug that such types of slow-release pharmaceuticals are not suitable for use with sparingly soluble drugs.

SUMMARY OF THE INVENTION

The present inventors conducted various studies in order to develop a process for preparing a slow-release pharmaceutical agent that is free from the aforementioned problems of the prior art products. As a result, the inventors have found that the duration of the sustained release of a pharmaceutically active substance can be extended significantly by employing fumaric acid and/or DL-tryptophan, both of which are low-molecular weight materials. However, it was found that no such prolonging effect could be attained by organic acids other than fumaric acid such as citric acid, maleic acid, succinic acid, tartaric acid and malic acid, or amino acids other than DL-tryptophan such as L-valine, L-tryptophan, DL-methionine, L-methionine, L-phenylalanine, L-isoleucine, L-leucine and L-glutamic acid.

DETAILED DESCRIPTION OF THE INVENTION

Figure 1:
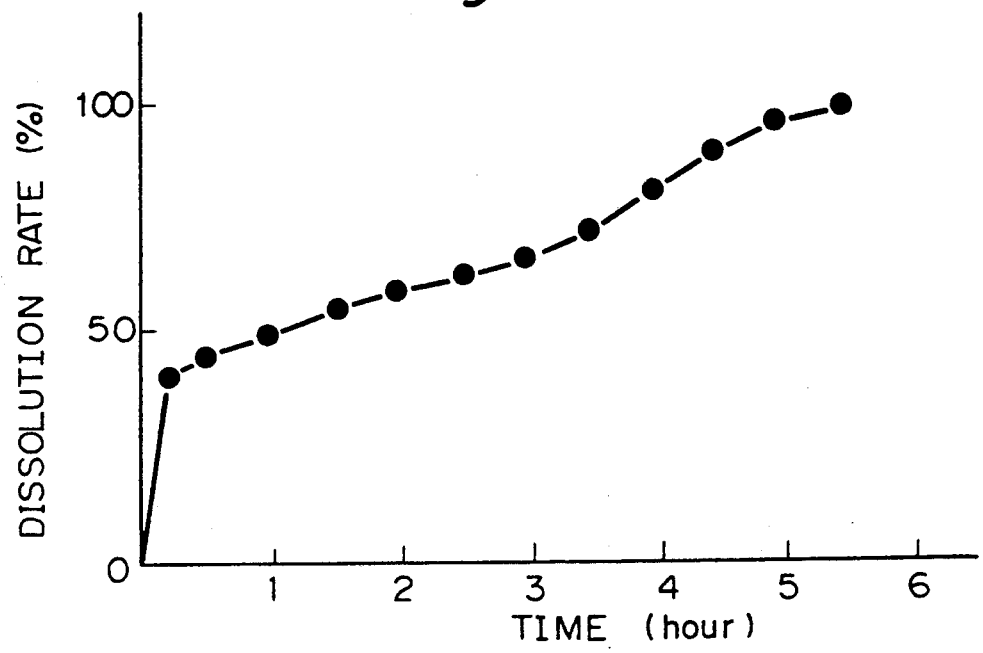
FIG. 1 depicts the dissolution profile of the layered tablets prepared in Example 1.

The slow-release pharmaceutical agent of the present invention is prepared by the following procedures: predetermined amounts of a pharmacologically active substance and an excipient are weighed; predetermined amount of fumaric acid and/or DL-tryptophan are weighed; and the individual components are mixed by routine method. The use of an excipient is optional but if one is used, preferable excipients are lactose, mannitol, inositol, calcium citrate, dibasic calcium phosphate, hardened oils, and stearic acid. The desirable effect of fumaric acid and/or DL-tryptophan is attained if they are used in an amount of at least 10% of the total weight of the pharmaceutical composition.

The slow-release pharmaceutical agent of the present invention may be used with practically all types of drugs such as hypotensives, antipyretic analgesic antiinflammatories, immunoregulators, adrenocortical hormones, antidiabetic agents, vasodilators, cardiotonics, antiarrhythmic agents, anti-arteriosclerotic agents and antidotes.

To the mixed powder containing the pharmacologically active substance, fumaric acid and/or DL-tryptophan and optionally an excipient, a lubricant such as magnesium stearate, calcium stearate or talc, and any other necessary components are added and the resulting mixture is compressed into tablets. If desired, the mixture may be worked into a dosage form suitable for implanting in the human body.

The mixed powder may also be blended with sucrose, a fragrance, a colorant and any other appropriate components and the resulting blend is then compressed to form troches of predetermined shapes. If desired, the blend may be formulated as a pharmaceutical for buccal administration.

A layer (A) containing a pharmaceutically active substance may be placed on another layer (B) containing no such active substance and the two layers then compressed together to form a double-layered tablet which achieves enhanced delivery of the effective substance after a given period of time has passed. Two modifications of this multiple-layered tablet are as follows: a tablet which is prepared by compressing a layer having the composition specified by the present invention and a fast-release layer containing the same pharmacologically active substance; and tablet prepared by compressing the following three layers together, the first layer having the composition specified by the present invention, the second layer consisting of fumaric acid and/or DL-tryptophan, and the third layer being a fast-release layer containing a pharmacologically active substance which is the same as what is present in the first layer.

The mixed powder described above may be blended with an appropriate binder, such as hydroxypropyl cellulose, hydroxypropyl methyl cellulose or corn starch, dissolved in either water or an organic solvent, and the blend granulated, dried and classified to obtain granules If desired, a granulation having this composition may be mixed with a fast-release granulation containing the same pharmacologically active substance. Slow-release enteric granules may be prepared by coating the first granulation with enteric bases such as hydroxypropyl methyl cellulose phthalate and carboxymethylethyl cellulose. These enteric slow-release granules may be mixed with fast-release granules containing the same pharmacologically active substance. Said first granulation may be coated with water-insoluble bases and the so coated granules may optionally be mixed with fast-release granules containing the same pharmacologically active substance. The fast-release granules containing a pharmacologically active substance may be coated with fumaric acid and/or DL-tryptophan to convert them into slow-release granules. If desired, these slow-release granules may be compressed to form slow-release tablets; mixtures of said granules with water-insoluble bases may be compressed into tablets; and the so formed tablets may be coated with enteric bases or water-insoluble bases. These tablets may be provided with a sugar coating which may optionally contain a pharmacologically active substance that is of the same type as incorporated in the center of the tablets. Core/shell type slow-release tablets may be prepared by compressing the aforementioned tablets after they have been coated with a fast-release composition containing the same pharmacologically active substance. In this case, a coat of fumaric acid/or DL-tryptophan may be provided between the core tablet and the shell of the fast-release composition. Any type of the aforementioned granules may be encapsulated to formulate capsules If desired, the aforementioned slow-release granules may be incorporated in suppository bases to form slow-release suppositories Alternatively, slow-release suppositories may be prepared by coating the aforementioned slow-release tablets with suppository bases.

Fumaric acid and DL- tryptophan to be incorporated in the slow-release pharmaceutical agent of the present invention may be used independently or in admixture of any appropriate proportions. By properly adjusting the mixing proportions of fumaric acid and DL-tryptophan, the dissolution rate of a pharmacologically active substance may be increased in an acidic environment and decreased in a near-neutral environment or vice versa. It is also possible to maintain a substantially constant dissolution rate at all pHs of the environment. Therefore, the drug release of the pharmaceutical agent of the present invention can be controlled by properly adjusting the ratio of fumaric acid to DL-tryptophan.

The slow-release pharmaceutical agent of the present invention releases its active substance as the fumaric acid and/or DL-tryptophan is slowly lost, so the pharmacologically active substance that can be incorporated may be water-soluble or sparingly water-soluble and is not limited to any particular type.

It should of course be understood that in putting the slow-release pharmaceutical agent of the present invention to use, colorants, flavoring agents, stabilizers and any other appropriate additives may be added as required.

The present invention is hereunder described in greater detail with reference to working examples and a reference example, to which the scope of the invention is by no means limited.

EXAMPLE 1

| Layered tablet | lower layer (mg) | middle layer (mg) | upper layer (mg) |
|---|---|---|---|
| Scopolamine hydrobromide | 0.2 | — | 0.1 |
| Fumaric acid | 60 | 25 | — |
| Calcium hydrogenphosphate (anhydrous) | 29.4 | 9.8 | — |
| Lactose | — | — | 24.7 |
| Crystalline cellulose | — | — | 10 |
| Calcium stearate | 0.4 | 0.2 | 0.2 |
| Total | 90 | 35 | 35 |

To 0.2 g of scopolamine hydrobromide, 29.4 g of calcium hydrogenphosphate (anhydrous) was added in small portions and well mixed in a mortar to form a triturate. The triturate (29.6 g) was well mixed with fumaric acid (60 g) and calcium stearate (0.4 g) in a polyethylene bag to form a mixed powder A.

Twenty-five grams of fumaric acid, 9.8 g of potassium hydrogenphosphate (anhydrous) and 0.2 g of calcium stearate were intimately mixed in a polyethylene bag to make a mixed powder B.

To 0.1 g of scopolamine hydrobromide, 10 g of crystalline cellulose was added in small portions and mixed well in a mortar to make a triturate. This triturate (10.1 g) was mixed well with 24.7 g of lactose and 0.2 g of calcium stearate in a polyethylene bag to make a mixed powder C.

Multilayer tableting was performed on a single-punch machine equipped with a die (8 mm$^\phi$) and flat-faced punches: first, 90 mg of the mixed powder A was placed in the die and precompressed lightly; 35 mg of the mixed powder B was placed on the first fill and lightly precompressed; thereafter, 35 mg of the mixed powder C was placed on the second fill and compressed with a total pressure of about 1.2 tons.

The resulting multiple-layered tablets had the dissolution profile depicted in FIG. 1 that was obtained by conducting a dissolution test with an apparatus of the type specified in "Method I (rotary basket method)", the Japanese Pharmacopoeia, 10th rev.; 500 ml of distilled water was used as a testing fluid and the basket was rotated at 100 rpm.

EXAMPLE 2

| Granules (per 100 mg) | |
|---|---|
| Indomethacin | 25 (mg) |
| DL-tryptophan | 35 |
| Hardened oil (hydrogenerate soybean oil) | 38 |
| Ethyl cellulose | 2 |
| Total | 100 |

A blender was charged with 750 g of indomethacin, 1,050 g of DL-tryptophan and 1,140 g of the hardened oil (hydrogenated soybean oil) and mixing was conducted for 10 minutes. Thereafter, 600 g of an ethanol solution of 10% ethyl cellulose (ETHOCEL 10CPS of Dow Chemical) was added and blending was conducted for an additional 10 minutes. The blend was granulated in a rotary granulator equipped with a net (1.0 mm$^\phi$), dried at 45° C. in a tray dryer for 6 hours, and classified on a 12-mesh sieve to make granules.

Figure 2:
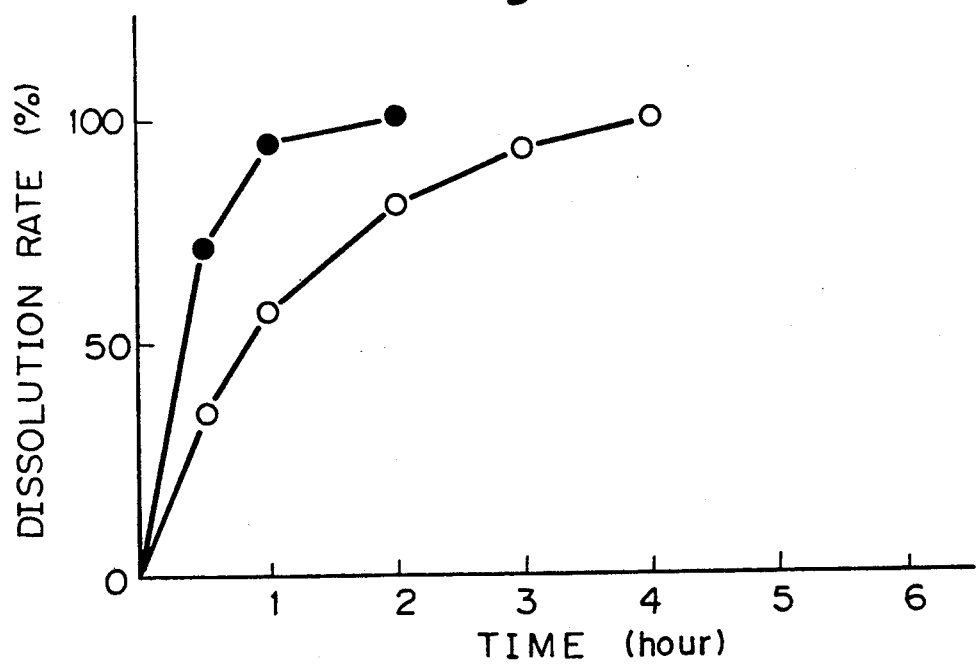
FIG. 2 depicts the dissolution profiles of the granules prepared in Example 2, the profile of dissolution in Fluid 1 being indicated by —•— and that in Fluid 2 indicated by —○—.

The granules had the dissolution profiles shown in FIG. 2 that were obtained by conducting a dissolution test on 100 mg of the granules with an apparatus of the type specified in "Method I (rotary basket method)", Japanese Pharmacopoeia, 10th rev.; 500 ml each of Fluid 1 (pH 1.2) and Fluid 2 (pH 6.8) was used as testing fluids and the basket was rotated at 100 rpm.

EXAMPLE 3

Figure 3:
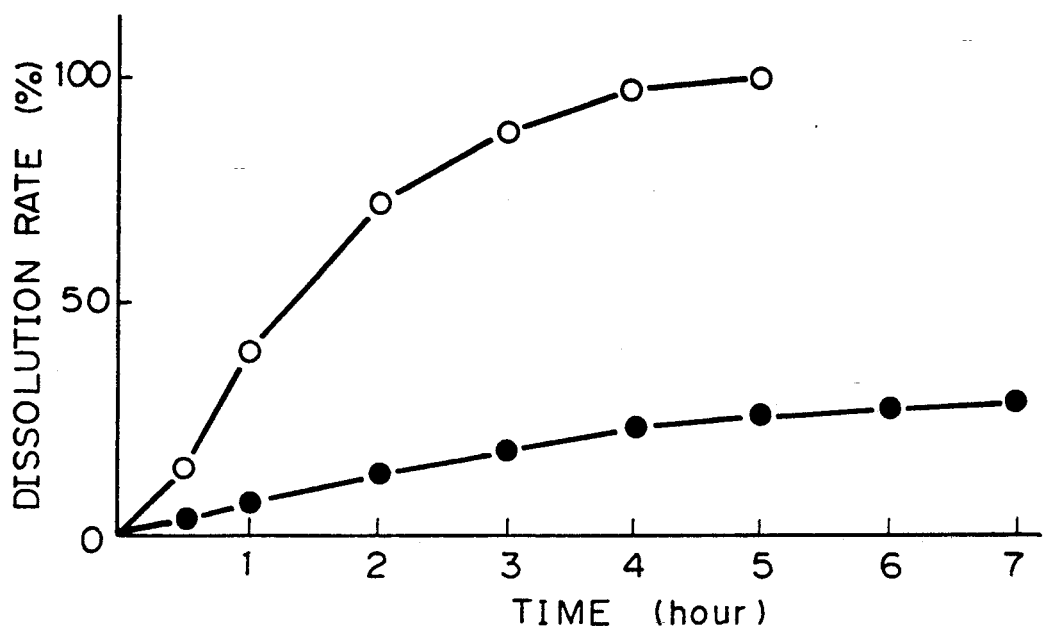
FIG. 3 depicts the dissolution profiles of the enteric granules prepared in Example 3, the profile of dissolution in Fluid 1 being indicated by —•— and that in Fluid 2 indicated by —○—.

Two thousand five hundred grams of the granules prepared in Example 2 were coated with 15% (w/w), based on the granules, of 6% hydroxypropyl methyl cellulose phthalate (HP-55 of Shinetsu Chemical Industry Co., Ltd.) dissolved in a 1:1 mixture of methylene chloride and ethanol. The coating machine used was a Flow Coater FLO-5 of Okawara Mfg. Co., Ltd. The so prepared enteric granules had the dissolution profiles depicted in FIG. 3 which were obtained by conducting a dissolution test on 115 mg of the enteric granules in accordance with the same method as employed in Example 2.

EXAMPLE 4

Three hundred grams of the granules prepared in Example 2 and 805 g of the enteric granules obtained in Example 3 were mixed in a polyethylene bag and charged in No. 2 capsules in such a manner that each capsule contained 110.5 mg of the mixed granules.

Figure 4:
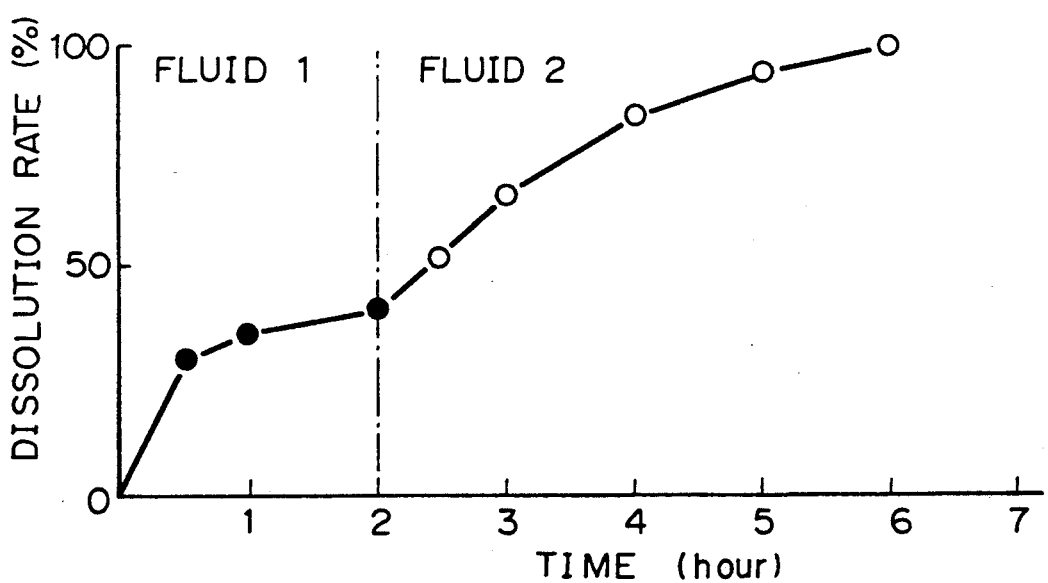
FIG. 4 depicts the dissolution profiles of the capsules prepared in Example 4, the profile of dissolution in Fluid 1 being indicated by —•— and that in Fluid 2 indicated by —○—.

The resulting capsules had the dissolution profile shown in FIG. 4 which was obtained by conducting a dissolution test as in Example 2 except that Fluid 1 was employed for the first two hours of the test while Fluid 2 was used thereafter.

EXAMPLE 5

| Tablet | |
|---|---|
| Phenobarbital | 1 (mg) |
| DL-tryptophan | 99 |
| Total | 100 |

To 1 g of phenobarbital, 99 g of DL-tryptophan was added in small amounts and mixed in a mortar. The mixed powder was fed into a single-punch tableting machine equipped with a die (7 mm$^\phi$) and flat-faced punches, and compressed at a total pressure of 1.5 tons so as to make tablets each weighing 100 mg.

Figure 5:
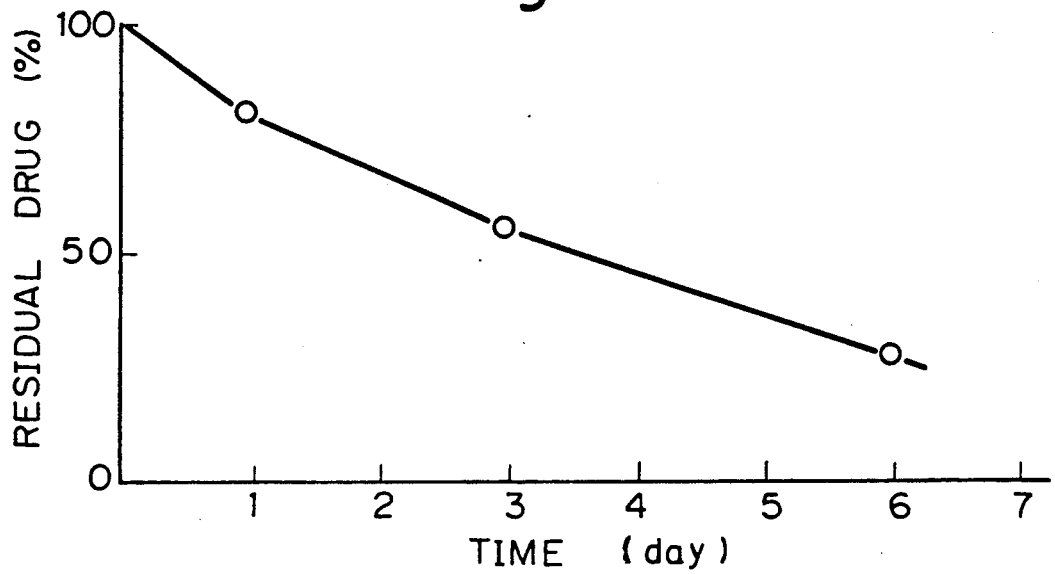
FIG. 5 depicts the dissolution profile of the tablets that were prepared in Example 5 and which were implanted under the dorsal skin of rats.

The time-dependent dissolution profile of the tablets implanted under the dorsal skin of rats is shown in FIG. 5. In obtaining the data shown in FIG. 5, the tablets were implanted at four different positions under the dorsal skin of each of the four rats tested and, at a predetermined intervals, the tablets were taken out of the rats and the residual amount of phenobarbital in each tablet was measured. No formation of fibers around the tablets was observed. After 14 days of implanting, there was no indication at all of the presence of phenobarbital or DL-tryptophan under the dorsal skin of the rats upon visual observation.

EXAMPLE 6

| Tablet | |
|---|---|
| Aminopyrine | 3 (mg) |
| Polyethylen glycol 6000 | 17 |
| DL-tryptophan | 25 |
| Total | 45 |

Aminopyrine (3 g), Polyethylene glycol 6000 (17 g) and DL-tryptophan (25 g) were well mixed in a polyethylene bag. The mixed powder was fed into a single-punch tableting machine equipped with an oval die (major axis, 8 mm; minor axis, 3 mm) and punches, and compressed at a total pressure of about 0.6 tons so as to make tablets weighing 45 mg each.

Comparative tablets were prepared by the same procedures except that DL-tryptophan was replaced by Polyethylene glycol 6000.

The tablets of the present invention and the comparative samples were administered to the rectum of five rats which had been fasted for 24 hours. The tablets were not excreted in the following 12 hours. On the next day, the tablets of the present invention were excreted in small amounts of the rats' feces but the rats to which the comparative tablets had been administered did not excrete the tablets and merely excreted a small amount of feces. The comparative tablets would have been dissolved away since they were not found in the digestive tracts of the autopsyed animals either.

The size of the tablets of the present invention had been reduced by about half their initial size and the residual aminopyrine content ,was 48.9+4.2%.

EXAMPLE 7

| Tablet | |
|---|---|
| Nicorandil | 10 (mg) |
| DL-tryptophan | 68.5 |
| Stearic acid | 10 |
| Hydroxypropyl cellulose | 1 |
| Magnesium stearate | 0.5 |
| Total | 90 |

A blender was charged with 3,425 g of DL-tryptophan and 500 g of stearic acid and mixing was conducted for 10 minutes. Thereafter, 500 g of an aqueous solution of 10% hydroxypropyl cellulose (NISSO HPC-L of Nippon Soda Co., Ltd.) and blending was conducted for an additional 10 minutes. The blend was granulated after passage through a 32-mesh sieve, dried at 45° C. in a tray dryer for 6 hours and classified on a 32-mesh sieve to obtain fine granules.

These fine granules (3,975 g ) were mixed well with 500 g of Nicorandil and 25 g of magnesium stearate in a polyethylene bag. The mixture was fed into a rotary tableting machine (Model RT-15-Hl of Kikusui Seisakusho, K.K.) equipped with a die (6 mm$\phi$) and sugar-coated round punches (radius, 4.5 mm), and compressed at a sufficient pressure to form tablets each weighing 90 mg.

Four thousand grams of the tablets were fed into a "Perfect coater" (Model PTC-10 of Okawara Mfg. Co., Ltd.) and treated with a coating solution of the following composition so that each tablet would be given a 10-mg coat.

| Coating solution | |
|---|---|
| Eudragit ® L30D | 1,500 g |
| Polyethylene glycol 6000 | 50 |
| Talc | 150 |
| Distilled water | 1,500 |
| Total | 3,200 |

Figure 6:
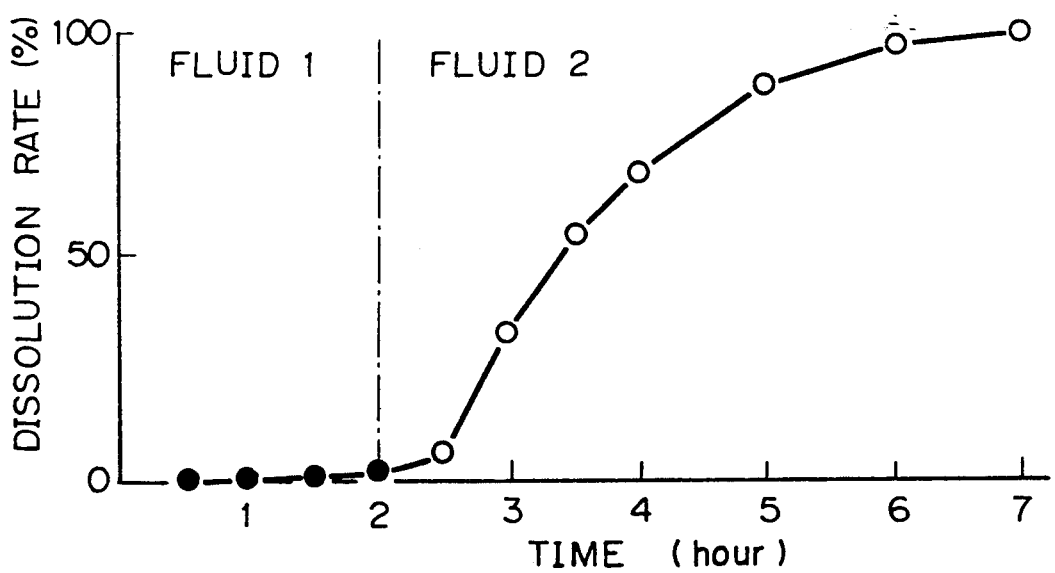
FIG. 6 depicts the dissolution profiles of the enteric tablets prepared in Example 7, the profile of dissolution in Fluid 1 being indicated by —•— and that in Fluid 2 indicated by —○—.

The resulting enteric tablets had the dissolution profile shown in FIG. 6 which was obtained by conducting a dissolution test as in Example 4.

EXAMPLE 8

| Tablet | |
|---|---|
| Acetylsalicylic acid | 100 (mg) |
| Fumaric acid | 100 |
| DL-tryptophan | 98 |
| Magnesium stearate | 2 |
| Total | 300 |

Acetylsalicylic acid (100 g), fumaric acid (100 g), DL-tryptophan (98 g) and magnesium stearate (2 g) were mixed in a polyethylene bag. The mixed powder was fed into a single-punch tableting machine equipped with a die (10 mm$\phi$) and flat-faced punches, and compressed at a total pressure of about 1.8 tons so as to form tablets each weighing 300 g.

Comparative tablets were formed by repeating the same procedures except that fumaric acid and DL-tryptophan were replaced by methyl cellulose (Metlose ® SM-8000 of Shinetsu Chemical Industry Co., Ltd.)

Figure 7:
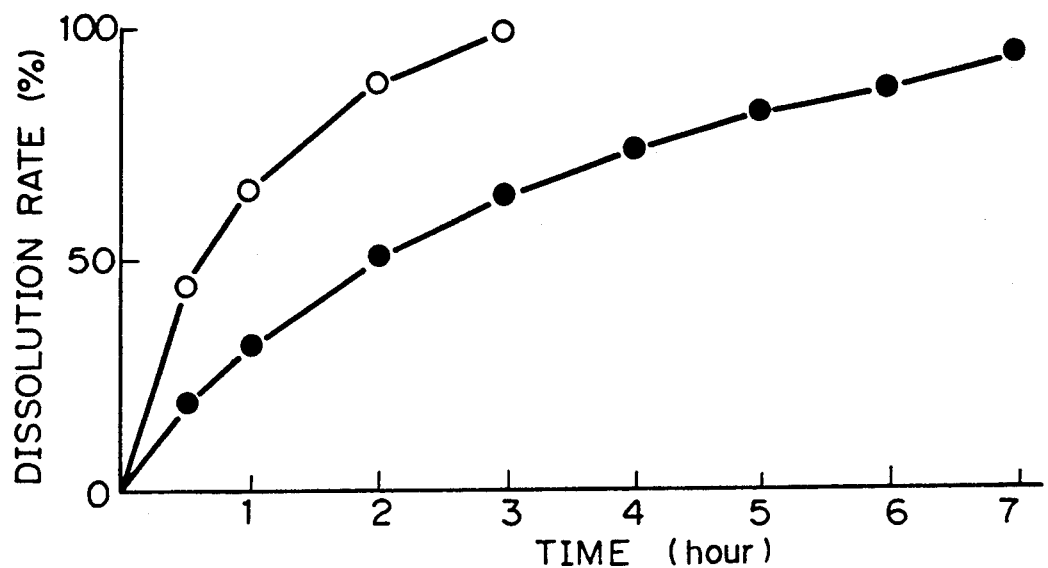
FIG. 7 depicts the dissolution profiles of the tablets prepared in Example 8 (—•—) and of the comparative tablets (—○—)

The two types of tablets had the dissolution profiles shown in FIG. 7 which were obtained by conducting a dissolution test with an apparatus of the type specified in the "Method of Disintegration Test", the Japanese Pharmacopoeia, 10th rev.; distilled water was used as a testing fluid.

In order to examine the stability of each type of tablet, an accelerated aging test was conducted by the following two methods: in one method, the tablets were put in stoppered glass containers and left to stand at 40° C. for 3 months; in the other method, the tablets were put in open glass containers and left to stand in a desiccator for 3 months at 40° C. and at 61.5% r.h. The results are shown in Table 1.

TABLE 1

| | Residual acetylsalicylic acid (%) | |
|---|---|---|
| | in stoppered containers | in desiccator 40° C., |
| Sample | 40° C., 3 months | 61.5% r.h., 3 months |
| tablets of the invention | 98.8% | 85.3% |
| comparative tablets | 76.5% | 41.4% |

Example 9

| Tablet | (a) | (b) | (c) |
|---|---|---|---|
| Isosorbitol nitrate | 20 (mg) | 20 (mg) | 20 (mg) |
| Fumaric acid | 90 | 70 | 50 |
| DL-tryptophan | 10 | 30 | 50 |
| Calcium citrate | 29 | 29 | 29 |
| Calcium stearate | 1 | 1 | 1 |
| Total | 150 | 150 | 150 |

Isosorbitol nitrate (20 g), fumaric acid (90 g), DL-tryptophan (10 g), calcium citrate (29 g) and calcium stearate (1 g) were mixed in a polyethylene bag. The mixed powder was fed into a single-punch tableting machine equipped with a die (8 mm⌀) and flat-faced punches, and compressed at a total pressure of about 1.2 tons so as to provide tablets each weighing 150 mg [Example 9-(a)].

Isosorbitol nitrate (20 g), fumaric acid (70 g), DL-tryptophan (30 g), calcium citrate (29 g) and calcium stearate (1 g) were mixed in a polyethylene bag. As in Example 9-(a), the mixed powder was compressed into tablets [Example 9-(b)].

Isosorbitol nitrate (20 g), fumaric acid (50 g), DL-tryptophan (50 g), calcium citrate (29 g) and calcium stearate (1 g) were mixed in a polyethylene bag. As in Example 9-(a), the mixed powder was compressed into tablets [Example 9-(c)].

Figure 8:
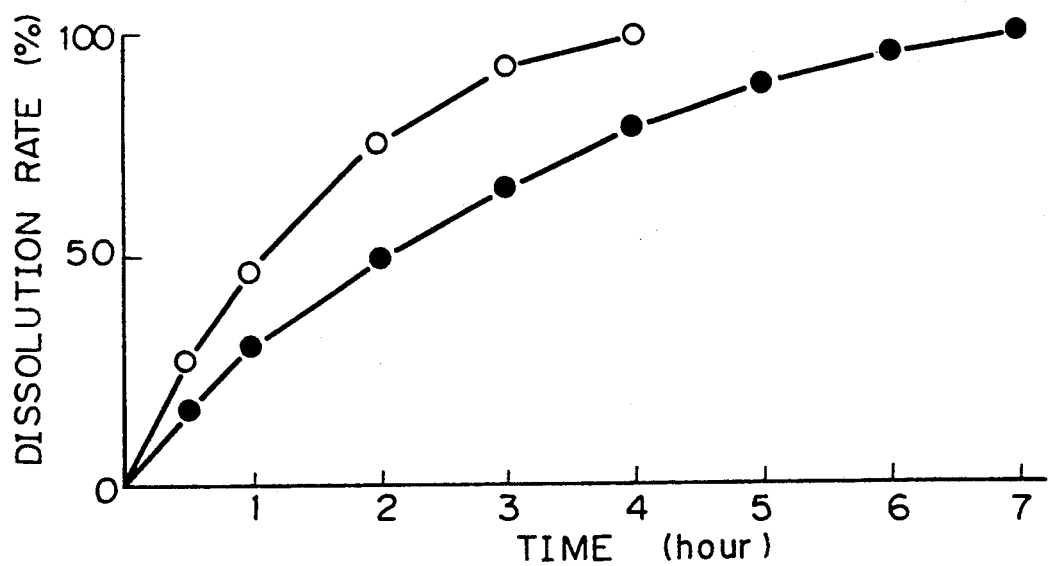
FIG. 8 depicts the dissolution profiles of the tablets prepared in Example 9-(a), the profile of dissolution in Fluid 1 being indicated by —•— and that in Fluid 2 indicated by —○—.
Figure 9:
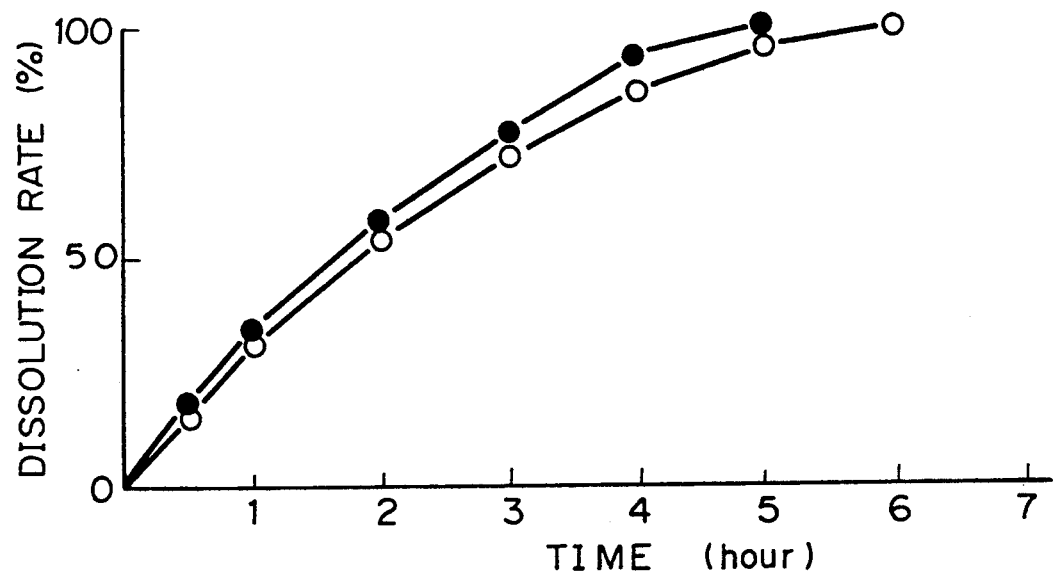
FIG. 9 depicts the dissolution profiles of the tablets prepared in Example 9-(b), the profile of dissolution in Fluid 1 being indicated by —•— and that in Fluid 2 indicated by —○—.
Figure 10:
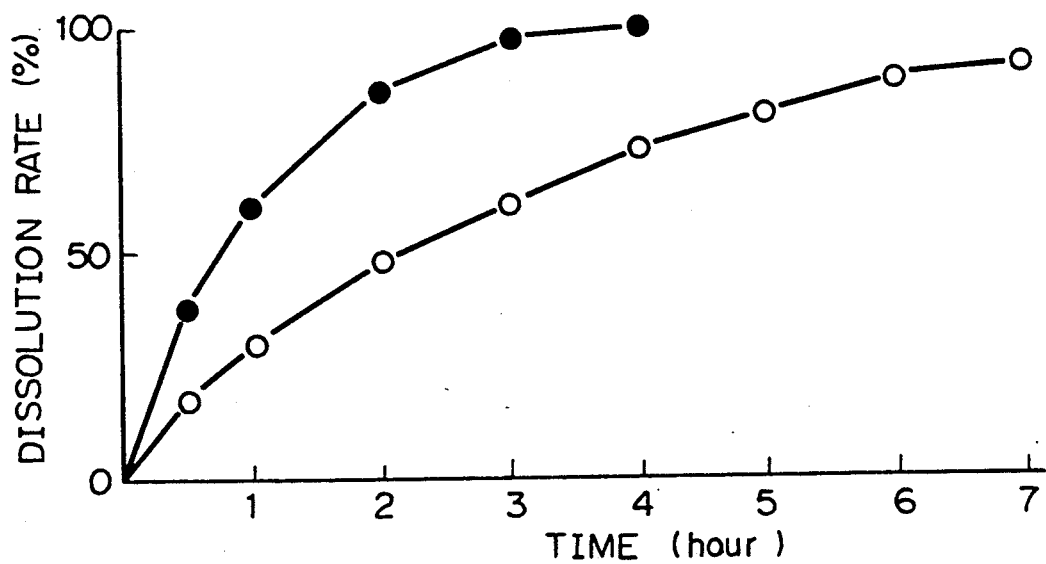
FIG. 10 depicts the dissolution profiles of the tablets prepared in Example 9-(c), the profile of dissolution in Fluid 1 being indicated by —•— and that in Fluid 2 indicated by —○—.

The tablets prepared in Examples 9-(a), 9-(b) and 9-(c) had the dissolution profiles shown in FIGS. 8, 9 and 10, respectively. The data shown in these figures were obtained by conducting dissolution tests with an apparatus of the type shown in "Method II (puddle method) of Dissolution Test", the Japanese Pharmacopoeia, 10th rev.; 500 ml each of Fluid 1 (pH≈1.2) and Fluid 2 (pH≈6.8) was used as testing solutions, and the puddle was rotated at 100 rpm.

The graphs in FIGS. 8 to 10 show that the rate of drug dissolution in the stomach or intestines can be freely controlled by adjusting the mixing proportions of fumaric acid and DL-tryptophan.

EXAMPLE 10

| Troche | |
|---|---|
| Chlorhexidine hydrochloride | 5 (mg) |
| Fumaric acid | 30 |
| DL-tryptophan | 122 |
| Hydroxypropyl cellulose | 3 |
| Total | 160 |

Chlorhexidine hydrochloride (5 g), fumaric acid (30 g) and DL-tryptophan (122 g) were well mixed in a mortar. Thereafter, 60 g of an aqueous solution of 5% hydroxypropyl cellulose (Nisso HPC-L of Nippon Soda Co., Ltd.) was added and intimate blending was conducted. The blend was granulated by sifting through a 14-mesh sieve, dried at 50° C. in a tray dryer for 4 hours, and crassified for 10 mesh. The granulation was fed into a single-punch tableting machine equipped with a die (8 mm⌀) and flat-faced punches, and compressed at a total pressure of about 1.5 tons so as to make troches each weighing 160 mg.

The so prepared troches melted slowly in the mouth and stayed there for about 3 hours.

EXAMPLE 11

| Tablet | |
|---|---|
| Nicorandil | 15 (mg) |
| Fumaric acid | 94 |
| DL-tryptophan | 40.5 |
| Magnesium stearate | 0.5 |
| Total | 150 |

Figure 11:
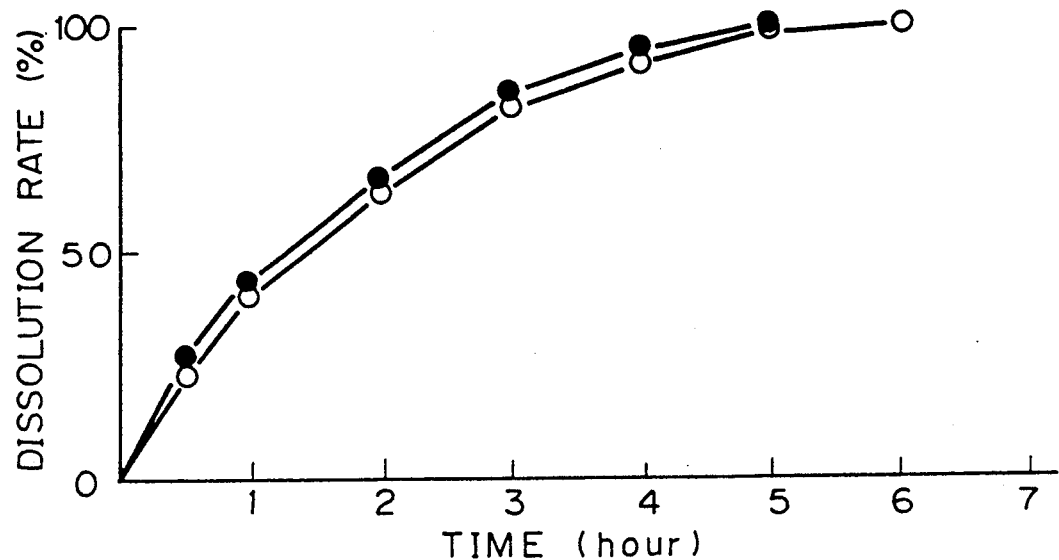
FIG. 11 depicts the dissolution profiles of the tablets prepared in Example 11, the profile of dissolution in Fluid 1 being indicated by —•— and that in Fluid 2 indicated by —○—.

Nicorandil (15 g), fumaric acid (94 g), DL-tryptophan (40.5 g) and magnesium stearate (0.5 g) were mixed in a polyethylene bag. The mixed powder was fed into a single-punch tableting machine equipped with a die (8 mm⌀) and flat-faced punches, and compressed at a total pressure of 1.2 tons so as to form tablets each weighing 150 mg. These tablets had the dissolution profile showing in FIG. 11 which was obtained by conducting a dissolution test as in Example 9.

EXAMPLE 12

| Suppository | |
|---|---|
| Aminopyrine | 50 (mg) |
| DL-tryptophan | 400 |
| Crystalline cellulose | 135 |
| Hydroxypropyl methyl cellulose | 15 |
| Novata E | 1,400 |
| Total | 2,000 |

Fifty grams of aminopyrine (under 35 mesh), 400 g of DL-tryptophan and 135 g of crystalline cellulose were mixed well in a mortar. Thereafter, 300 g of an aqeuous solution of 5% hydroxypropyl methyl cellulose (TC-5-E of Shinetsu Chemical Industry Co., Ltd.) was added and blended with the previously obtained mixture.

The resulting blend was granulated in a rotary granulator equipped with a net (0.7 mm⌀) The granules were spheroidized with a Marumerizer machine (Model Q-236 of Fuji Powdal K.K.), dried at 50° C. in a tray dryer for 4 hours and classified on a 12-mesh sieve to obtain pellets.

One hundred and forty grams of Novata E (Henkel Corporation) was melted at 60° C. and 60 g of the above prepared pellets were dispersed in the melt. The resulting dispersion was cast into a mold and cooled slowly to form suppositories each weighing 2 g.

| Comparative sample | |
|---|---|
| Aminopyrine | 50 (mg) |
| Novata E | 1,950 |
| Total | 2,000 |

Novata E (195 g), a suppository base sold by Henkel & Cie GmbH, was melted at 60° C. and 5 g of aminopyrine was dispersed. The dispersion was cast into a mold and cooled slowly to form suppositories each weighing 2 g.

Figure 12:
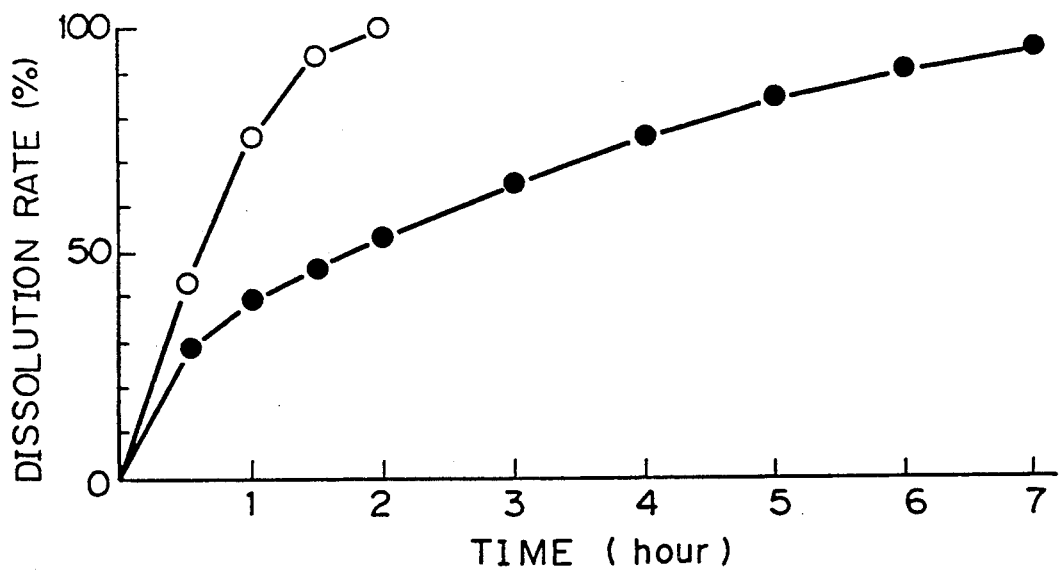
FIG. 12 depicts the dissolution profiles of the suppositories prepared in Example 12 (—•—) and of the comparative suppositories (—○—)

The two types of suppositories had the dissolution profiles shown in FIG. 12 which were obtained by the following procedures: in a cell in a suppository release testing apparatus (Model TMS-103 of Toyama Sangyo K.K.), 3 ml of Fluid 2 (pH≈6.8) and one suppository were placed and agitated at 25 rpm; in the release phase, 300 ml of Fluid 2 (pH≈6.8) was placed and stirred at 100 rpm; both the cells and the release phase were held at 37°±0.1° C. while the amount of aminopyrine that dissolved in the release phase was measured at predetermined intervals.

| Reference Example Dissolution Profile of Tablets for Different Ratios of Fumaric Acid to DL-Tryptophan | | | | | | | |
|---|---|---|---|---|---|---|---|
| Sample No. | 1 | 2 | 3 | 4 | 5 | 6 | 7 |
| Formulation | | | | | | | |
| Fumaric acid (mg) | 100 | 80 | 70 | 60 | 40 | 20 | 0 |
| DL-tryptophan (mg) | 0 | 20 | 30 | 40 | 60 | 80 | 100 |
| Total (mg) | 100 | 100 | 100 | 100 | 100 | 100 | 100 |

Tablet Preparation

Fumaric acid and DL-tryptophan were well mixed at the proportions shown above. Each of the resulting mixed powders was fed into a single-punch machine equipped with a die (7.0 mm$^\phi$) and flat-faced punches, and compressed at a total pressure of 1 ton so as to make tablets each weighing 100 mg.

Measurement of Dissolving Time

Measurement were conducted in accordance with the "Method of Disintegration Test", the Japanese Pharmacopoeia, 10th rev., and the time required for the tablets in the tester to disappear was used as the dissolution time. No auxiliary disk was used in the measurements. Three testing fluids were used: Fluid 1 (pH$\simeq$1.2), Fluid 2 (pH$\simeq$6.8), and distilled water.

Results

In Fluid 1 (pH$\simeq$1.2), the dissolution rate slowed down as the content of fumaric acid increased. In Fluid 2 (pH$\simeq$6.8), the dissolution rate decreased sharply as the content of DL-tryptophan increased. This shows that by properly controlling the mixing proportions of fumaric acid and DL-tryptophan, the drug dissolution rate can be adjusted to any desirable value that fits the pH of a given environment. Another observation was that at a certain ratio of fumaric acid to DL-tryptophan, the dissolution time was constant irrespective of the pH of the testing fluids. This indicates the possibility of attaining a constant dissolution time notwithstanding the change in the pH of a given environment.

Figure 13:
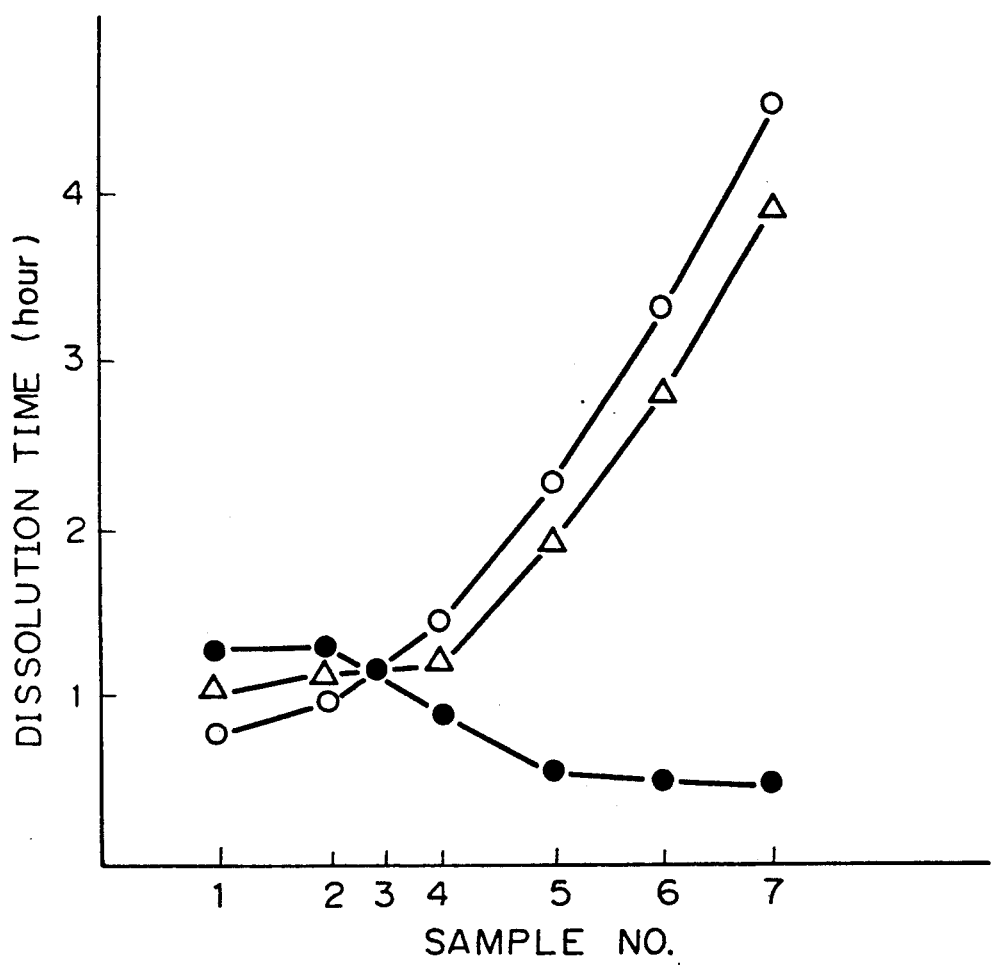
FIG. 13 depicts the dissolution profiles of the tablets prepared in the Reference Example, the profile of dissolution in Fluid 1 being indicated by —•—, that in Fluid 2 indicated by —○—, and that in distilled water indicated by —Δ—.

The results of the disintegration test conducted as above on the individual tablets (sample Nos. 1–7) are graphed in FIG. 13.

We claim:

1. A slow-release pharmaceutical agent which consists essentially of fumaric acid and/or DL-tryptophan in addition to one or more pharmacologically active substances, provided that the combination of Nicorandil and fumaric acid is excluded, wherein said slow-release pharmaceutical agent is a layered table consisting of a layer containing a pharmacologically active substance and a layer which does not contain any pharmaceutically active substance.

2. A slow-release multiple-layered tablet which is prepared by compressing a first layer of a slow-release pharmaceutical agent which consists essentially of DL-tryptophan and/or at least 20% fumaric acid in addition to one or more pharmacologically active substances, provided that the combination of Nicorandil and fumaric acid is excluded, and a fast-release layer containing the same pharmacologically active substance as present in the first layer.

3. A slow-release multiple-layered tablet which is prepared by compressing a first layer formed of a slow-release pharmaceutical agent which consists essentially of fumaric acid and/or DL-tryptophan in addition to one or more pharmacologically active substances, provided that the combination of Nicorandil and fumaric acid is excluded, a second layer composed of fumaric acid and/or DL-tryptophan, and a fast-release third layer containing the same pharmacologically active substance as present in the first layer.

4. A slow-release granule composed of a granulation coated with an enteric base, said granulation being composed of a slow-release pharmaceutical agent which consists essentially of DL-tryptophan and/or at least 20% fumaric acid in addition to tone or more pharmacologically active substances, provided that the combination of Nicorandil and fumaric acid is excluded.

5. A slow-release granule comprising a first granulation which is coated with an enteric base and which is composed of a slow-release pharmaceutical agent which consists essentially of fumaric acid and/or DL-tryptophan in addition to one or more pharmacologically active substances, provided that the combination of Nicorandil and fumaric acid is excluded, and a fast-release second granulation containing the same pharmacologically active substance as present in the first granulation.

6. A slow-release granule comprising a granulation coated with a water-insoluble base, said granulation comprising a slow-release pharmaceutical agent which comprises fumaric acid and/or DL-tryptophan in addition to one or more pharmacologically active substances, provided that the combination of Nicorandil and fumaric acid is excluded.

7. A slow-release granule comprising a first granulation coated with a water-insoluble base, said first granulation comprising a slow-release pharmaceutical agent which consists essentially of DL-tryptophan and/or at least 20% fumaric acid in addition to one or more pharmacologically active substances, provided that the combination of Nicorandil and fumaric acid is excluded, and a fast-release second granulation containing the same pharmacologically active substance as present in the first granulation.

8. A slow-release granule formed of a fast-release granulation comprising a pharmacologically active substance, said granulation being coated with a coating consisting essentially of fumaric acid and/or DL-tryptophan, provided that the combination of Nicorandil and fumaric acid is excluded.

9. A slow-release tablet prepared by compressing a granulation comprising a slow-release pharmaceutical agent which consists essentially of fumaric acid and/or DL-tryptophan in addition to one or more pharmacologically active substances, provided that the combination of Nicorandil and fumaric acid is excluded, said granulation being coated with an enteric base.

10. A slow-release tablet prepared by compressing a slow-release granulation comprising a slow-release pharmaceutical agent which consists essentially of fumaric acid and/or DL-tryptophan in addition to one or more pharmacologically active substances, provided that the combination of Nicorandil and fumaric acid is excluded, together with a fast-release granulation containing the same pharmaceutically active substance as present in the slow-release granulation, said slow-release tablet being coated with an enteric base.

11. A slow-release tablet prepared by compressing a powder comprising a slow-release pharmaceutical agent which consists essentially of DL-tryptophan and/or at least 20% fumaric acid in addition to one or more pharmacologically active substances, provided that the combination of Nicorandil and fumaric acid is excluded, said tablet being coated with an enteric base.

12. A slow-release tablet prepared by compressing a granulation comprising a slow-release pharmaceutical agent which consists essentially of DL-tryptophan and/or at least 20% fumaric acid in addition to one or more pharmacologically active substances, provided that the combination of Nicorandil and fumaric acid is excluded, said granulation being coated with a water-insoluble base.

13. A slow-release tablet prepared by compressing a slow-release granulation comprising a slow-release pharmaceutical agent which consists essentially of fumaric acid and/or DL-tryptophan in addition to one or more pharmacologically active substances, provided that the combination of Nicorandil and fumaric acid is excluded, together with a fast-release granulation containing the same pharmaceutically active substance as present in the slow-release granulation, said slow-release tablet being coated with a water-insoluble base.

14. A slow-release tablet prepared by compressing a powder comprising a slow-release pharmaceutical agent which consists essentially of fumaric acid and/or DL-tryptophan in addition to one or more pharmacologically active substances, provided that the combination of Nicorandil and fumaric acid is excluded, said tablet being coated with a water-insoluble base.

15. A sugar-coated slow-release tablet prepared by compressing a granulation comprising a slow-release pharmaceutical agent which consists essentially of fumaric acid and/or DL-tryptophan in addition to one or more pharmacologically active substances, provided that the combination of Nicorandil and fumaric acid is excluded, said granulation being surrounded by a sugar coating.

16. A sugar-coated slow-release tablet prepared by compressing a slow-release granulation comprising a slow-release pharmaceutical agent which consists essentially of fumaric acid and/or DL-tryptophan in addition to one or more pharmacologically active substances, provided that the combination of Nicorandil and fumaric acid is excluded, together with a fast-release granulation containing the same pharmaceutically active substance as present in the slow-release granulation, said slow-release tablet being surrounded by a sugar coating.

17. A sugar-coated slow-release tablet prepared by compressing a powder comprising a slow-release pharmaceutical agent which consists essentially of fumaric acid and/or DL-tryptophan in addition to one or more pharmacologically active substances, provided that the combination of Nicorandil and fumaric acid is excluded, said tablet being surrounded by a sugar coating.

18. A sugar-coated slow-release tablet according to claim 15 wherein said sugar coating contains the same pharmacologically active substance as is present in said slow-release pharmaceutical agent.

19. A sugar-coated slow-release tablet according to claim 16 wherein said sugar coating contains the same pharmacologically active substance as is present in said slow-release pharmaceutical agent.

20. A sugar-coated slow-release tablet according to claim 17 wherein said sugar coating contains the same pharmacologically active substance as is present in said slow-release pharmaceutical agent.

21. A core/shell slow-release tablet wherein the core is a compressed tablet which consists essentially of fumaric acid and/or DL-trypptophan in addition to one or more pharmacologically active substances, provided that the combination of Nicorandil and fumaric acid is excluded, with a shell being compressed around said core tablet, said shell comprising a fast-release composition containing the same pharmacologically active substance as present in said core tablet.

22. A core/shell slow-release tablet wherein the core is a tablet having a composition which consists essentially of fumaric acid and/or DL-tryptophan in addition to one or more pharmacologically active substances, provided that the combination of Nicorandil and fumaric acid is excluded, with two shells being compressed around said core tablet, the first shell around said core tablet being made of fumaric acid and/or DL-tryptophan, and the second shell around said first shell being made of a fast-release composition containing the same pharmacologically active substance as present in said core tablet.

23. A process for preparing a slow-release granule which comprises applying a coat consisting essentially of DL-tryptophan and/or at least 20 wt % fumaric acid to at least one pharmacologically active substance, provided that the combination of Nicorandil and fumaric acid is excluded.

24. A slow-release suppository wherein a table consisting essentially of a compressed composition of fumaric acid and/or DL-tryptophan in addition to one or more pharmacologically active substances, provided that the combination of Nicorandil and fumaric acid is excluded, is coated with a suppository base.

25. A process for preparing a slow-release pharmaceutical agent which comprises providing a composition consisting essentially of fumaric acid in addition to at least one pharmacologically active substance excluding Nicorandil, and formulating said composition in dosage form.

26. A process for preparing a slow-release pharmaceutical agent which comprises providing a composition consisting essentially of at least one pharmacologically active substance including Nicorandil together with DL-tryptophan or both DL-tryptophan and at least 20 wt % fumaric acid, and formulating said composition in a dosage form.

27. A process for preparing a slow-release pharmaceutical agent which comprises providing a composition consisting essentially of fumaric acid and/or DL-tryptophan in an amount of at least 20 wt % of the composition in addition to at least one pharmacologically active substance, provided that the combination or Nicorandil and fumaric acid is excluded, and formulating said composition in a dosage form, wherein said composition is formulated as a layered tablet consisting of a layer containing pharmacologically active substance and a layer which does not contain any pharmacologically active substance.

28. A process for preparing a slow-release multiple layered tablet which comprises providing a composition consisting essentially of fumaric acid and/or DL-tryptophan in an amount of at least 20 wt % of the composition in addition to at least one pharmacologically active substance, provided that the combination or Nicorandil and fumaric acid is excluded, and formulating said composition in a dosage form, by compressing a slow-release layer of said composition and a fast-release layer containing the same pharmacologically active substance as present in the first layer.

29. A process for preparing a slow-release multiple-layered tablet which comprises compressing a layer consisting essentially of fumaric acid and/or DL-tryptophan in addition to at least one pharmacologically active substance, provided that the combination of Nicorandil and fumaric acid is excluded, a slow-release layer composed of fumaric acid and/or DL-tryptophan, and a fast-release layer containing the same pharmacologically active substance as present in the first layer.

30. A process for preparing a slow-release pharmaceutical composition which comprises providing a composition consisting essentially of fumaric acid and/or DL-tryptophan in addition to at least one pharmacologically active substance, provided that the combination of Nicorandil and fumaric acid is excluded, wherein fumaric acid and/or DL-tryptophan is present in an amount of at least 20 wt % of the total weight of the composition, and formulating said composition in a dosage form as a slow-release granule, and applying a coating of an enteric base.

31. A process for preparing a slow-release pharmaceutical composition which comprises providing a composition consisting essentially of fumaric acid and/or DL-tryptophan in addition to at least one pharmacologically active substance, provided that the combination of Nicorandil and fumaric acid is excluded, wherein fumaric acid and/or DL-tryptophan is present in an amount of at least 20 wt % of the total weight of the composition, and formulating said composition in a dosage form and applying a coat of water-insoluble base.

32. A process for preparing a slow-release tablet which comprises providing a composition consisting essentially of fumaric acid and/or DL-tryptophan in addition to at least one pharmacologically active substance, provided that the combination of Nicorandil and fumaric acid is excluded, wherein fumaric acid and/or DL-tryptophan is present in an amount of at least 20 wt % of the total weight of the composition, and formulating said composition in a dosage form by compressing said composition so as to form a tablet, then coating said tablet with an enteric base.

33. A process for preparing a slow-release pharmaceutical composition which comprises providing a composition consisting essentially of fumaric acid and/or DL-tryptophan in addition to at least one pharmacologically active substance, provided that the combination of Nicorandil and fumaric acid is excluded, wherein fumaric acid and/or DL-tryptophan is present in an amount of at least 20 wt % of the total weight of the composition, and formulating said composition in a dosage form and applying a coat of water-insoluble base, then coating said tablet with a water insoluble base.

34. A process for preparing a sugar-coated slow-release tablet which comprises providing a composition consisting essentially of DL-tryptophan in addition to at least one pharmacologically active substance, provided that the combination of Nicorandil and fumaric acid is excluded, wherein fumaric acid and/or DL-tryptophan is present in an amount of at least 20 wt % of the total weight of the composition, and formulating said composition in a dosage form by compression to form a center tablet, then optionally coating said tablet with a water-insoluble base or an enteric base, and then coating with a sugar coat.

35. A process according to claim 34 wherein said sugar coat contains the same pharmacologically active substance as present in the center table.

36. A process for preparing a core/shell slow-release tablet which comprises providing a composition consisting essentially of fumaric acid and/or DL-tryptophan in addition to at least one pharmacologically active substance, provided that the combination of Nicorandil and fumaric acid is excluded, wherein fumaric acid and/or DL-tryptophan is present in an amount of at least 20 wt % of the total weight of the composition, and formulating said composition in a dosage form by compression to form a tablet, then compressing a shell around the core tablet, said shell being made of a fast-release composition containing the same pharmacologically active substance as is present in said core tablet.

37. A process for preparing a core/shell slow-release tablet which comprises providing a composition consisting essentially of fumaric acid and/or DL-tryptophan in addition to at least one pharmacologically active substance, provided that the combination of Nicorandil and fumaric acid is excluded, wherein fumaric acid and/or DL-tryptophan is present in an amount of at least 20 wt % of the total weight of the composition, and formulating said composition in a dosage form by compression to form a tablet, then compressing first and second shells around the core tablet, the first shell around said core tablet being made of fumaric acid and/or DL-tryptophan, and a second shell around said first shell being made of a fast-release composition containing the same pharmacologically active substance as present in said core tablet.

38. A process for preparing a slow-release suppository which comprises providing a composition consisting essentially of fumaric acid and/or DL-tryptophan in addition to at least one pharmacologically active substance, provided that the combination of Nicorandil and fumaric acid is excluded, wherein fumaric acid and/or DL-tryptophan is present in an amount of at least 20 wt % of the total weight of the composition, and formulating said composition in a dosage form by compressing said composition to form a slow-release tablet, then coating said tablet with a suppository base.

* * * * *

UNITED STATES PATENT AND TRADEMARK OFFICE
CERTIFICATE OF CORRECTION

PATENT NO. : 5,188,840
DATED : Feb. 23, 1993
INVENTOR(S) : Yoshimitsu IIDA It is certified that error appears in the above-identified patent and that said Letters Patent is hereby corrected as shown below:

Column 11, Line 42, delete "table" and insert therefore --tablet--.

Signed and Sealed this

Thirtieth Day of November, 1993

Attest:

BRUCE LEHMAN

*Attesting Officer*  *Commissioner of Patents and Trademarks*